| United States Patent [19] | [11] Patent Number: 4,714,080 |
|---|---|
| Edgar, Jr. et al. | [45] Date of Patent: Dec. 22, 1987 |

[54] METHOD AND APPARATUS FOR NONINVASIVE MONITORING OF ARTERIAL BLOOD OXYGEN SATURATION

[75] Inventors: Reuben W. Edgar, Jr.; Dennis W. Gilstad; Ronald L. Branstetter, all of San Antonio, Tex.

[73] Assignee: Nippon Colin Co., Ltd., Komaki, Japan

[21] Appl. No.: 915,688

[22] Filed: Oct. 6, 1986

[51] Int. Cl.$^4$ .............................................. A61B 5/00
[52] U.S. Cl. .................................... 128/633; 128/666
[58] Field of Search ................................ 128/633, 666

[56] References Cited

U.S. PATENT DOCUMENTS

| 4,167,331 | 9/1979 | Nielson | 128/633 |
|---|---|---|---|
| 4,266,554 | 5/1981 | Hamaguri | 128/633 |
| 4,407,290 | 10/1983 | Wilber | 128/633 |
| 4,586,513 | 5/1986 | Hamaguri | 128/633 |
| 4,621,643 | 11/1986 | New et al. | 128/633 |

OTHER PUBLICATIONS

EP-102-816-A, New et al., published Mar. 1984.

*Primary Examiner*—William E. Kamm
*Assistant Examiner*—John C. Hanley
*Attorney, Agent, or Firm*—Gary W. Hamilton

[57] ABSTRACT

A noninvasive optical oximeter for measuring oxygen saturation of arterial blood. A sample of blood is illuminated with light at two different wavelengths. Light reflected by the blood is sensed by a photodetector and an output signal is created in response thereto. The output signal is processed to form a quotient representing the AC components of the reflected light at each wavelength. The oxygen saturation of the blood is calculated by correlating this quotient with an oxygen saturation reference curve uniquely representative of the blood oxygen saturation characteristics of a particular individual.

17 Claims, 6 Drawing Figures

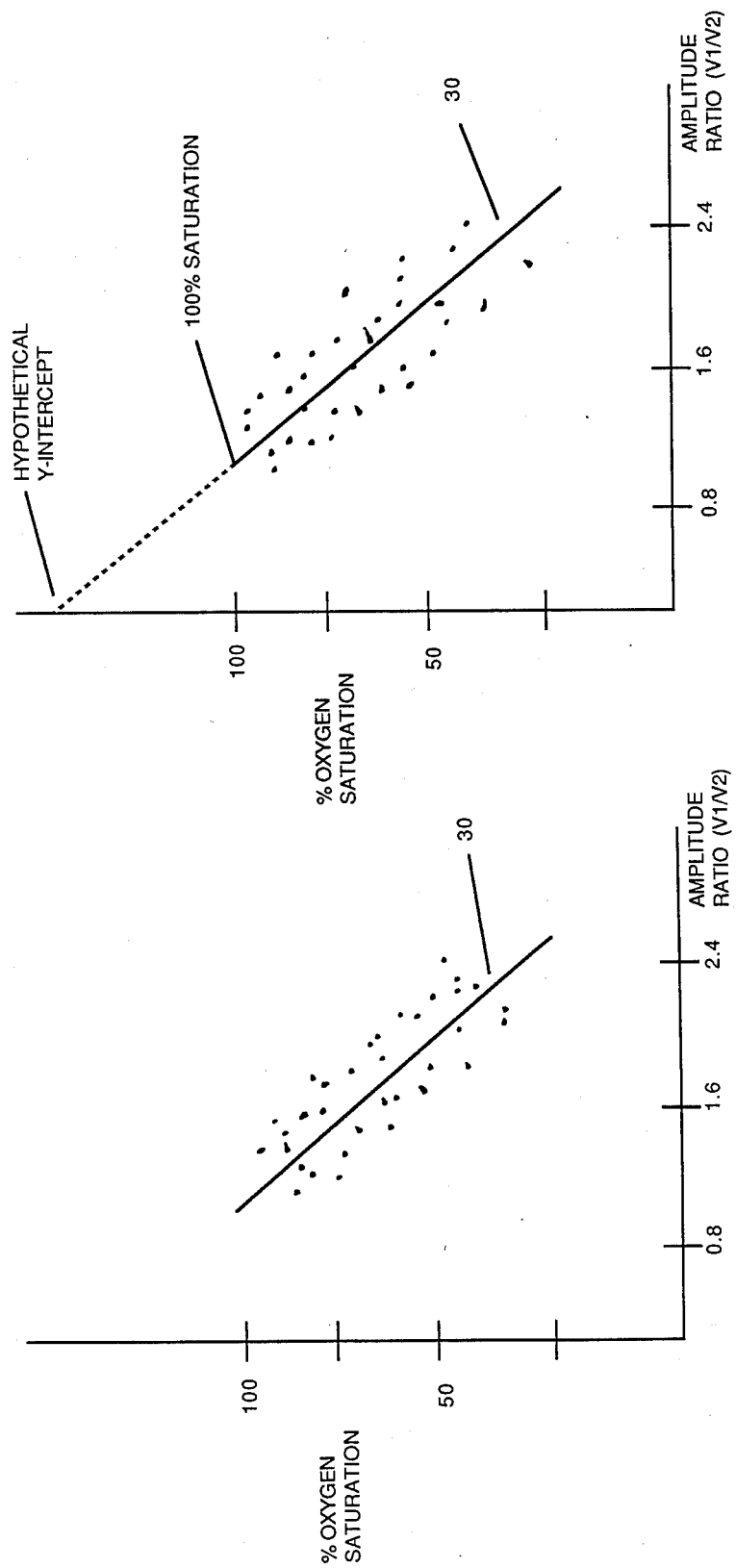

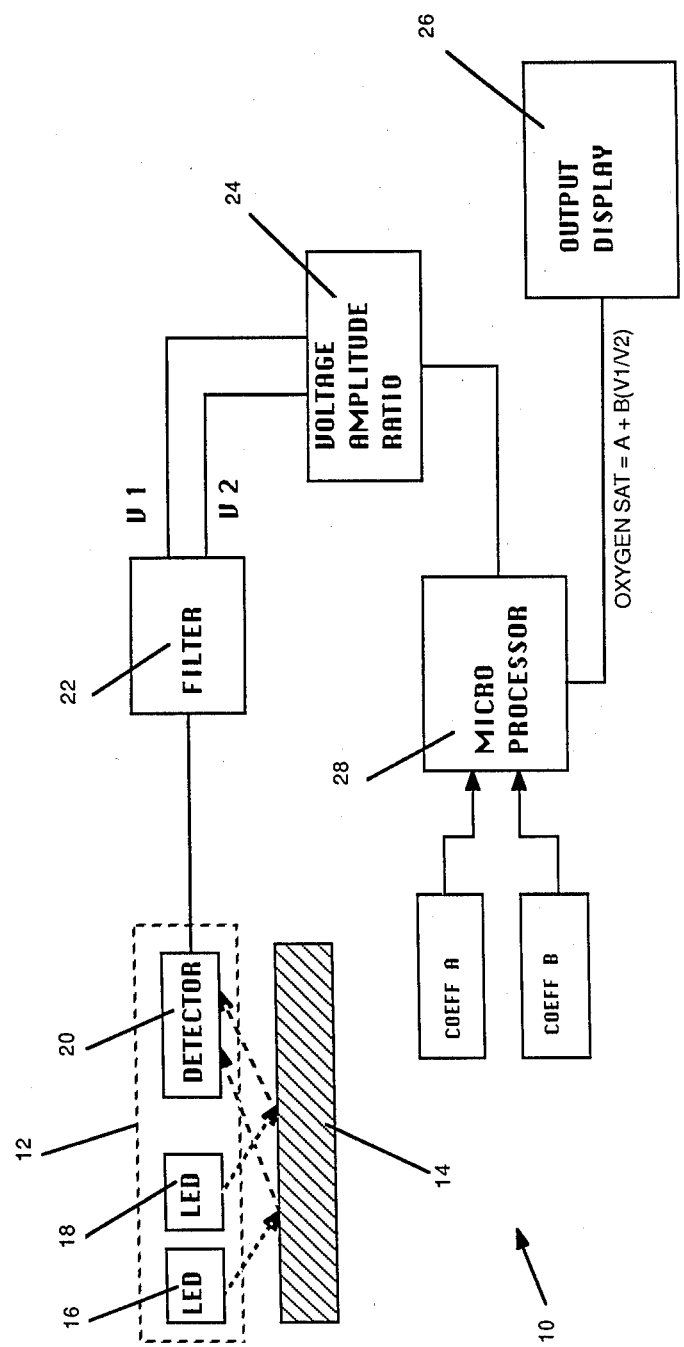

METHOD AND APPARATUS FOR NONINVASIVE MONITORING OF ARTERIAL BLOOD OXYGEN SATURATION

FIELD OF THE INVENTION

The present invention relates generally to an oximeter which can be used to estimate the degree of oxygen saturation of arterial blood. More specifically, the present invention provides a noninvasive reflectance oximeter which can be automatically calibrated to calculate a patient's blood oxygen saturation by correlating light reflected by the patient's blood with a reference oxygen saturation curve for the particular patient.

BACKGROUND

Hemoglobin oxygen saturation (OS) of blood is defined as the ratio of the oxyhemoglobin ($HbO_2$) concentration to the total hemoglobin (Hb) concentration. One of the most common methods for measuring blood OS requires removal and analysis of a sample of the patient's blood. Analysis of an actual sample of blood is still considered the most accurate method for obtaining a reading of absolute blood oxygen saturation. However, this method is undesirable in cases where it is necessary to monitor blood oxygen saturation over long periods of time.

In many clinical situations, it is extremely important to be able to obtain continuous measurements of tissue oxygenation. While it is desirable to have an absolute measure of OS, it is often sufficient to measure relative changes in the blood oxygen saturation. For example, in the operating room, the physician is typically concerned only with significant changes in the patient's OS, and is less concerned with the measurement of absolute OS. In this situation, a noninvasive oximeter which is capable of detecting significant changes in the blood oxygen content would be especially useful.

It is well known that hemoglobin and oxyhemoglobin have different optical absorption spectra and that this difference in absorption spectra can be used as a basis for an optical oximeter. Most of the currently available oximeters using optical methods to determine blood oxygen saturation are based on transmission oximetry. These devices operate by transmitting light through an appendage such as a finger or an earlobe. By comparing the characteristics of the light transmitted into one side of the appendage with that detected on the opposite side, it is possible to compute oxygen concentrations. The main disadvantage of transmission oximetry is that it can only be used on portions of the body which are thin enough to allow passage of light.

There has been considerable interest in recent years in the development of an oximeter which is capable of using reflected light to measure blood oxygen saturation. A reflectance oximeter would be especially useful for measuring blood oxygen saturation in portions of the patient's body which are not well suited to transmission measurements. Experimental results suggest that it is possible to obtain accurate indications of blood oxygen content through the use of reflectance techniques.

A theoretical discussion of a basis for the design of a reflectance oximeter is contained in "Theory and Development of a Transcutaneous Reflectance Oximeter System for Noninvasive Measurements of Arterial Oxygen Saturation," by Yitzhak Mendelson (Published Doctoral Dissertation), No. 8329355, University Microfilms, Ann Arbor, Mi. (1983). A theoretical discussion of the optical properties of blood is found in "Optical Scattering in Blood," by Narayanan R. Pisharoty, (Published Doctoral Dissertation), No. 7124861, University Microfilms, Ann Arbor, Mi. (1971).

Numerous other works have disclosed theoretical approaches for analyzing the behavior of light in blood and other materials. The following is a brief list of some of the most relevant of these references: "New Contributions to the Optics of Intensely Light-Scattering Materials, Part 1," by Paul Kubelka, Journal of the Optical Society of America, Volume 38, No. 5, May 1948; "Optical Transmission and Reflection by Blood," by R. J. Zdrojkowski and N. R. Pisharoty, IEEE Transactions on Biomedical Engineering, Vol. BME-17, No. 2, April 1970; and "Optical Diffusion in Blood," by Curtis C. Johnson, IEEE Transactions on Biomedical Engineering, Vol. BME-17, No. 2, April 1970.

Various methods and apparati for utilizing the optical properties of blood to measure blood oxygen saturation have been shown in the patent literature. Representative devices for utilizing the transmission method of oximetry have been disclosed in U.S. Pat. Nos. 4,586,513; 4,446,871; 4,407,290; 4,226,554; 4,167,331; and 3,998,550. In addition, reflectance oximetry devices and techniques are shown generally in U.S. Pat. Nos. 4,447,150; 4,086,915; and 3,825,342.

Despite the advances shown in the above-mentioned references, the prior art is still lacking a satisfactory noninvasive reflectance oximeter which can be used to estimate blood oxygen saturation. In particular, there is a need for a noninvasive reflectance oximeter which can be quickly and easily calibrated to calculate a patient's arterial blood oxygen saturation. The method and apparatus of the present invention, as described hereinbelow, fulfills this need.

SUMMARY OF THE INVENTION

In the preferred embodiment of the present invention, the blood oxygen saturation of a patient's arterial blood is determined by a noninvasive optical technique which takes advantage of differences in the absorption spectra of hemoglobin and oxyhemoglobin. In its simplest form, the invention comprises means for illuminating the patient's arterial blood with light at two different wavelengths, means for measuring the intensity of the reflected light after contact with the blood and means for correlating the intensity of the reflected light with an oxygen saturation reference curve to determine the oxygen saturation of the patient's blood. One of the sources of light is at a wavelength for which the absorption coefficients of hemoglobin and oxyhemoglobin are approximately equal. The second source of light is at a wavelength for which the absorption coefficients for hemoglobin and oxyhemoglobin differ greatly from one another.

The reflected light signal detected by the system comprises an alternating-current (AC) component and a direct-current (DC) component for each of the respective light sources. The AC components of each of the reflected signals is filtered from the output of the sensor and a voltage amplitude ratio is calculated. This ratio is then correlated with an oxygen saturation reference curve to obtain an indication of the oxygen saturation of the patient's arterial blood.

The oxygen saturation curve used in the present system is constructed without the need to collect large quantities of empirical data for each particular patient.

One point on the reference curve can be calculated using a number of known constants relating to the optical properties of blood. This point is a Y-intercept corresponding to a hypothetical condition of greater than 100% oxygen saturation. The second point is a 100% oxygen saturation point which is obtained by taking reference measurements while the patient breathes pure oxygen for a short period of time. The hypothetical Y-intercept is a term which is fairly constant for different individuals. The slope of the reference curve, however, tends to vary for different individuals. By determining the second point on the reference curve for each individual using the method described above, it is possible to obtain an oxygen saturation reference curve which is uniquely representative of the oxygen saturation characteristics of the particular individual.

BRIEF DESCRIPTION OF THE DRAWINGS

FIG. 2 is a graphical representation of an oxygen saturation curve obtained by performing regression analysis of data obtained from the monitoring system shown in FIG. 1.

FIG. 3 is a graphical representation of the data shown in FIG. 2 showing the oxygen reference curve extrapolated to a hypothetical Y-intercept corresponding to an oxygen saturation of greater than 100%.

FIG. 5 is a schematic block diagram of a preferred embodiment of the noninvasive blood oxygen saturation monitoring system shown in FIG. 1 incorporating means for comparing the voltage amplitude ratio of the reflected signals to one of the oxygen saturation reference curves shown in FIG. 4.

DETAILED DESCRIPTION OF THE PREFERRED EMBODIMENT

Figure 1:
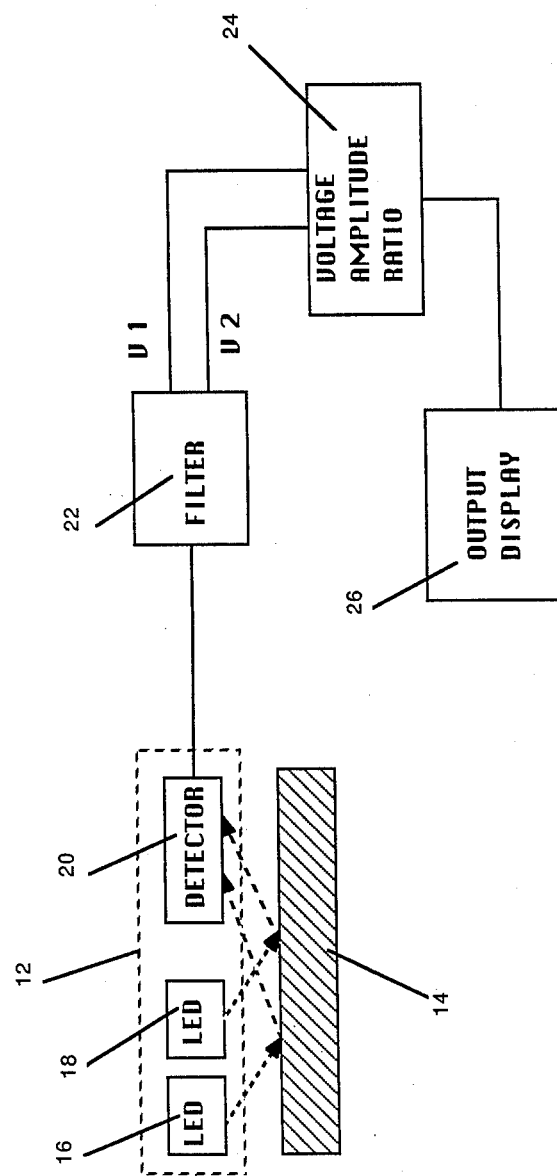
FIG. 1 is a schematic block diagram of a simplified embodiment of the noninvasive blood oxygen saturation monitoring system of the present invention.

Referring to the drawings in more detail, the noninvasive monitoring system 10 of the present invention is shown in its preferred embodiment. The simplest embodiment of the system is shown in FIG. 1. A monitoring probe 12 is positioned over a portion of the patient's tissue 14 such that light produced by two light emitting diodes (LED) 16 and 18 will be reflected by arterial blood in the tissue and detected by a photodetector 20. In the preferred embodiment, the LED 16 emits light having a wavelength of 660 nm (red) and the LED 18 emits light having a wavelength of 900 nm (infrared). However, the invention is not intended to be limited to any specific wavelength of light produced by the above-mentioned LEDs. Proper operation of the invention requires only that one source of light have a wavelength for which the absorption coefficients of hemoglobin and oxyhemoglobin are approximately equal and that the second source of light have a wavelength for which these absorption coefficients are different from one another. In an alternate embodiment of the invention, each of the LEDs could be replaced with an appropriate source of laser radiation providing monochromatic light at the desired wavelengths.

The output of the photodetector 20 will be an electrical signal representing a combination of direct-current (DC) and alternating-current (AC) components of the light reflected by the arterial blood in the tissue 14. This output signal is processed by an appropriate filter 22 to produce signals corresponding to the AC voltage components of each of the wavelengths of incident light. These AC voltage signals are then processed by a voltage amplitude ratio circuit 24 and displayed on an appropriate output device 26.

The functional features of the above-described system components can be accomplished through the use of electronic components and techniques which are well known in the art. For example, U.S. Pat. No. 4,447,150, issued to Heinemann, which by this reference is incorporated for all purposes, shows a system for illuminating a sample of blood with light at two wavelengths and for detecting light signals reflected by the blood. In addition, a system for obtaining electrical representations of the AC components of the reflected signals is shown in U.S. Pat. No. 4,586,513, issued to Hamaguri, which by this reference is incorporated for all purposes.

The use of the AC component of the reflected signal offers significant advantages for correlating the signals with blood oxygen saturation. As blood volume increases during systole, more light is absorbed by the blood and a decrease in skin reflectance can be observed. During diastole, skin blood volume increases and a proportional increase in the reflected light intensity can be observed. In general, the amplitude ratio of the AC components of the reflected signals will not be significantly affected by fixed light absorbers, such as bone, hair and skin pigmentation.

Experimental results obtained using the technique outlined above suggest that it is possible to establish a linear correlation between the amplitude ratio of the reflected signals and blood oxygen saturation. Based on empirical data it is possible to establish a correlation satisfying the following regression equation:

$$O_2 \text{ Saturation} = A - B \cdot (I_r/I_{ir}) \qquad \text{(Eq. 1)}$$

where:
  A and B are regression coefficients for the correlating line;
  $I_r$ is the relative intensity of the AC component of the backscattered red light; and
  $I_{ir}$ is the relative intensity of the AC component of the backscattered infrared light.

The intensity ratio can be related to the voltage ratio by the following relationship:

$$I_r/I_{ir} = (V_{D\ r} - V_{S\ r})/(V_{D\ ir} - V_{S\ ir}) \qquad \text{(Eq. 2)}$$

Where:
  $V_{D\ r}$ = Voltage measured at diastolic pulse for red light;
  $V_{D\ ir}$ = Voltage measured at diastolic pulse for for infrared light;
  $V_{S\ r}$ = Voltage measure at systolic pulse for red light; and
  $V_{S\ ir}$ = Voltage measured at systolic pulse for infrared light.

As was mentioned above, these equations for blood oxygen saturation are obtained by using standard statistical techniques to fit a regression curve to empirical data. An example of a hypothetical set of data yielding such a curve is shown in FIG. 2, where $V_1$ and $V_2$ represent the numerator and denominator, respectively, of Eq. 2.

As can be seen in FIG. 2, the data defines a generally linear curve 30 which conforms to the relationship defined in Eq. 1. Once the curve 30 shown in FIG. 2 has been calculated on the basis of empirical data, it is possible to calculate subsequent OS readings by simply measuring the amplitude ratio of the reflected signals and correlating this ratio with the reference curve. It is important to note that the oxygen saturation curve 30 shown in FIG. 2 is based on empirical data obtained from repeated measurements on the same individual. Alternatively, data taken from a large number of individuals can be averaged to obtain the regression curve. However, such a curve will be much less accurate than a curve constructed for a particular individual.

If the curve shown in FIG. 2 were extended upward as shown below in FIG. 3, it would pass through a point corresponding to 100% OS and would intercept the Y-axis at a point corresponding to a hypothetical condition of blood OS greater than 100%. While this point has no physical meaning, experimental data has shown that the hypothetical Y-intercept (regression coefficient A) tends to be fairly constant for different individuals. The slope of the regression curve, however, tends to vary for different individuals.

The calibration method of the present invention eliminates the need for empirical data by providing a means for mathematically calculating the regression coefficients used to construct the blood oxygen saturation curve for a particular patient. Specifically, the hypothetical Y-intercept, A, can be calculated using Eq. 3 shown below and the 100% saturation point can be determined by taking a measurement after the patient has been breathing pure oxygen for a short period of time.

Calculation of Y-intercept:

$$A = [(K_B \cdot W_{Dr})/(35 \cdot H_B \cdot K_{Dr} (W_{Or} - W_{Rr}))] + [W_{Rr}/(W_{Rr} - W_{Or})] \quad \text{(EQ. 3)}$$

Where:

$K_B$ = Scattering due to blood;

$K_{Dr}$ = Scattering due to tissue and blood at diastolic pulse for wavelength 660 nm;

$H_B$ = Fraction of blood volume containing hemoglobin;

$W_{Dr}$ = Absorption due to tissue and blood at diastolic pulse for wavelength 660 nm;

$W_{Rr}$ = Absorption coefficient for reduced hemoglobin for wavelength 660 nm; and $W_{Or}$ = Absorption coefficient for oxygenated hemoglobin for wavelength 660 nm.

It has been shown experimentally that the first term in Eq. 3 is very small in magnitude and can be ignored without causing significant error in the calculation of the Y-intercept, A. The second term is composed of the absorption coefficients for oxygenated and reduced hemoglobin at a known wavelength, for example 660 nm (red). These values are known constants which are related to the wavelength of light used to illuminate the blood. Therefore, the Y-intercept can be calculated by substituting the values of these absorption coefficients in the second term of Eq. 3. As an example, for light at 660 nm, the value for $W_{Rr}$ will be 1.732 and the value for $W_{Or}$ will be 0.211. By substituting these values in the second term of Eq. 3, the hypothetical Y-intercept is calculated to be 113%.

A second point on the blood oxygen saturation curve can be obtained by measuring the 100% saturation point for the particular patient. This point, which defines the slope of the oxygen saturation curve 32, is determined by measuring the voltage amplitude ratio of the reflected light after the patient breathes pure oxygen for a short period of time.

Figure 4A:
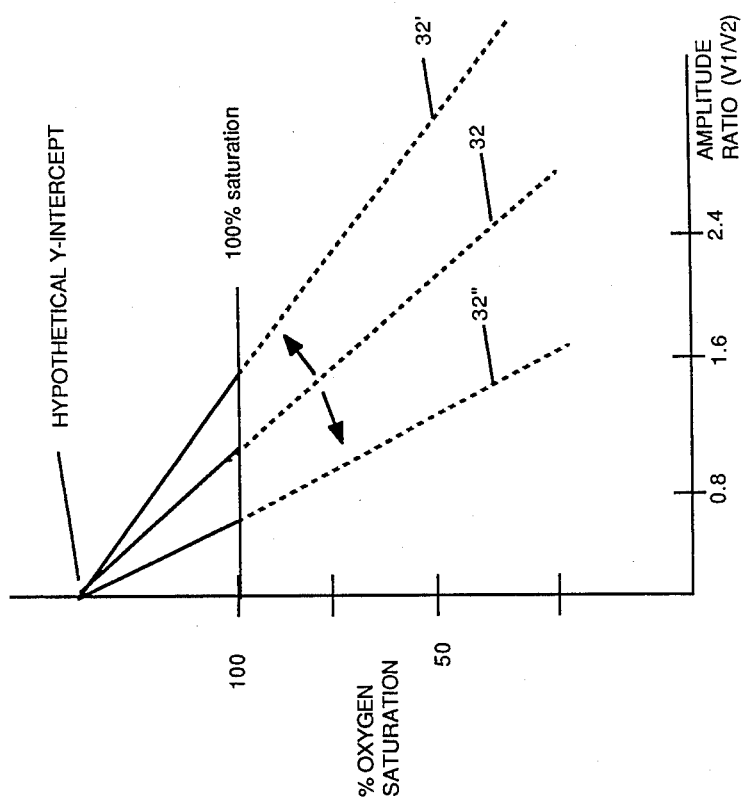
FIG. 4a is a family of oxygen saturation reference curves formed by the method of the present invention with each curve having a unique slope corresponding to a particular individual.
Figure 4:
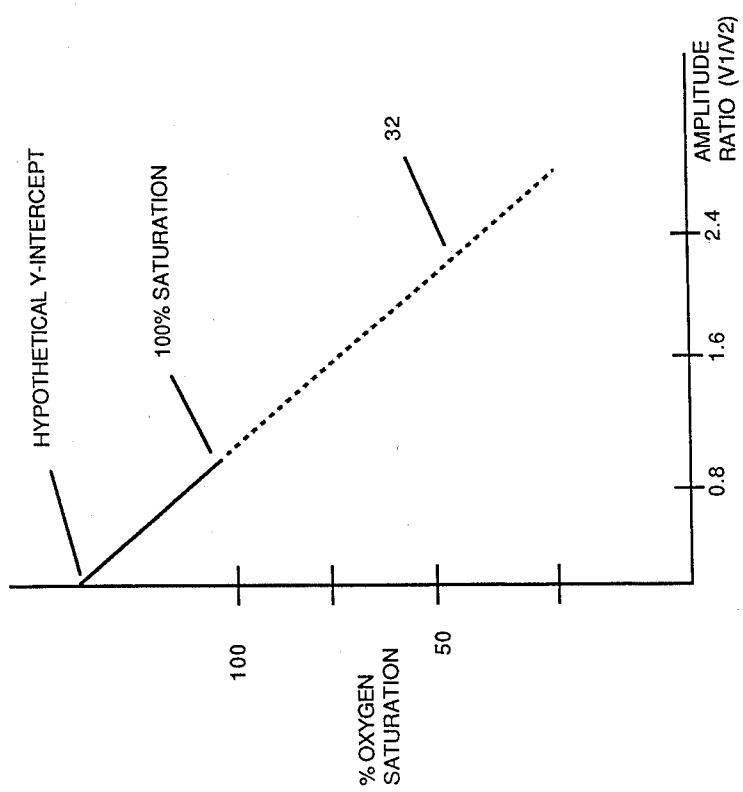
FIG. 4 is a graphical representation of an oxygen saturation reference curve formed by extrapolation techniques using the mathematical relationships provided by the method of the present invention.

From these two points, an oxygen saturation reference curve 32 can be extrapolated downward as shown in FIG. 4. Once this reference curve has been constructed, the patient's blood oxygen saturation can be determined by simply measuring the amplitude ratio of reflected light signals and correlating this ratio with the curve 32 to determine the corresponding blood oxygen saturation.

As was mentioned above, the slope, B, of the oxygen saturation curve tends to vary from one individual to another. FIG. 4a shows a family of hypothetical oxygen saturation curves 32, 32', and 32" with each of the curves having a unique slope determined by the blood properties of a particular individual.

A noninvasive monitoring system using the coefficients calculated by the method of the present invention is shown generally in FIG. 5. The system contains the same basic components of the simplified system shown in FIG. 1. However, the output of the voltage amplitude ratio circuit is provided, along with regression coefficients A and B, to a microprocessor 28 which calculates the oxygen saturation using the regression equations and mathematical relationships shown in Eqs. 1 through 3. The monitoring system shown in FIG. 5 can be constructed using components and techniques which are known in the art, such as those shown in the above-mentioned patents which have been incorporated by reference.

While the invention method and apparatus for noninvasive monitoring of arterial blood oxygen saturation has been described in connection with the preferred embodiment, it is not intended to be limited to the specific form set forth herein, but on the contrary, it is intended to cover such alternatives, modifications and equivalents as may be reasonably included within the spirit and scope of the invention as defined by the appended claims.

We claim:

1. A blood oxygen saturation monitoring system comprising:

a first source of electromagnetic radiation at a first wavelength;

a second source of electromagnetic radiation at a second wavelength;

means for positioning said first and second sources of electromagnetic radiation to illuminate a sample of blood;

sensing means for receiving electromagnetic radiation reflected by said sample of blood, said reflected electromagnetic radiation comprising an AC component and a DC component, said sensing means producing an output signal corresponding only to the AC components of the reflected portions of said first and second electromagnetic radiation;

means for producing a quotient of said AC voltage components; and means for calculating blood oxygen saturation by correlating said quotient of said AC voltage components with an oxygen saturation reference curve, said reference curve being uniquely representative of the blood oxygen saturation characteristics of a particular individual.

2. The monitoring system according to claim 1, wherein said first and second sources of electromagnetic radiation respectively comprise first and second light emitting diodes.

3. The monitoring system according to claim 2, wherein said first light emitting diode emits light having a wavelength corresponding to red, and said second light emitting diode emits light having a wavelength corresponding to infrared.

4. The monitoring system according to claim 3, wherein said reference curve is defined by first and second data points, said first data point comprising a quotient calculated using optical properties of blood for said first wavelength, said second data point being a unique oxygen saturation point for said particular individual.

5. The monitoring system according to claim 4, wherein said first data point is defined by the quotient $W_{Rr}/(W_{Rr}-W_{Or})$, wherein $W_{Rr}$ is the absorption coefficient for reduced hemoglobin for red light and $W_{Or}$ is the absorption coefficient for oxygenated hemoglobin for red light.

6. The monitoring system according to claim 5, wherein said second data point is defined by a unique 100% blood oxygen saturation point for said particular individual.

7. A blood oxygen saturation monitoring system comprising:
a first light emitting diode for producing light at a first wavelength;
a second light emitting diode for producing light at a second wavelength;
means for positioning said first and second light emitting diodes to illuminate a sample of blood;
sensing means for receiving light reflected by said sample of blood, said reflected light comprising an AC component and a DC component, said sensing means producing an output signal corresponding only to the AC components of said reflected light at said first and second wavelengths means for producing a quotient of said AC voltage components; and
means for calculating blood oxygen saturation by correlating said quotient of said AC voltage components with an oxygen saturation reference curve, said reference curve being defined by a linear relationship between first and second data points, said first data point corresponding to a quotient of absorption coefficients of blood for light at said first wavelength, said second data point being a unique blood oxygen saturation point for a particular individual.

8. The monitoring system according to claim 7, wherein said first light emitting diode provides light having a wavelength corresponding to red, and said second light emitting diode provides light having a wavelength corresponding to infrared.

9. The monitoring system according to claim 8, wherein said first wavelength of light is approximately 660 nm, and said second wavelength of light is approximately 900 nm.

10. The monitoring system according to claim 8, wherein said first data point is defined by the quotient $W_{Rr}/(W_{Rr}-W_{Or})$, wherein $W_{Rr}$ is the absorption coefficient for reduced hemoglobin for red light and $W_{Or}$ is the absorption coefficient for oxygenated hemoglobin for red light.

11. The monitoring system according to claim 10, wherein said second data point is defined by a unique 100% blood oxygen saturation point for said particular individual.

12. A method for determining the oxygen saturation of arterial blood, comprising the steps of:
illuminating a sample of said blood with electromagnetic radiation at a first wavelength;
illuminating said sample of blood with electromagnetic radiation at a second wavelength;
collecting electromagnetic radiation reflected by said sample of blood, said reflected radiation comprising an AC component and a DC component, and developing therefrom an electrical signal representing only the AC components of said reflected radiation at said first and second wavelengths;
processing said electronic signal to form a quotient corresponding to a voltage amplitude ratio of the alternating current components of said reflected radiation at said first and second wavelengths; and
calculating the percent of oxygen saturation of said sample of blood by correlating said voltage amplitude ratio with an oxygen saturation reference curve, said reference curve being uniquely representative of the blood oxygen saturation characteristics of a particular individual.

13. The method according to claim 12, wherein said steps of illuminating said radiation at said first and second wavelengths comprises the step of energizing first and second light emitting diodes, respectively.

14. The method according to claim 13, wherein said first and second wavelengths of light are approximately 660 nm and 900 nm, respectively.

15. The method according to claim 13, wherein said reference curve defined by a linear relationship between first and second data points, said first data point corresponding to a quotient of absorption coefficients of blood for light at said first wavelength, said second data point being a unique blood oxygen saturation point for a particular individual.

16. The method according to claim 15, wherein said first data point is determined by the quotient $W_{Rr}/(W_{Rr}-W_{Or})$, wherein $W_{Rr}$ is the absorption coefficient for reduced hemoglobin for red light and $W_{Or}$ is the absorption coefficient for oxygenated hemoglobin for red light.

17. The monitoring system according to claim 16, wherein said second data point is determined by the 100% blood oxygen saturation point for a particular individual.

* * * * *